United States Patent

Nielsen

[11] Patent Number: 6,001,832
[45] Date of Patent: Dec. 14, 1999

[54] [1,2,4]TRIAZOLO[4,3-A]QUINOXALINONE DERIVATIVES, THEIR PREPARATION AND USE

[75] Inventor: Flemming Elmelund Nielsen, Virum, Denmark

[73] Assignee: Novo Nordiskals, Bagsvaerd, Denmark

[21] Appl. No.: 08/809,055

[22] PCT Filed: Sep. 12, 1995

[86] PCT No.: PCT/DK95/00364

§ 371 Date: Mar. 7, 1997

§ 102(e) Date: Mar. 7, 1997

[87] PCT Pub. No.: WO96/08492

PCT Pub. Date: Mar. 21, 1996

[30] Foreign Application Priority Data

Sep. 16, 1994 [DK] Denmark .................... 1065/94

[51] Int. Cl.⁶ .............. C07D 487/04; A61K 31/495
[52] U.S. Cl. .............. 514/250; 514/232.5; 514/81; 514/228.5; 514/233.2; 514/224.8; 544/346; 544/354; 544/356; 544/115; 544/81; 544/57; 544/58.2; 544/58.6
[58] Field of Search ............ 514/81, 250, 232.5, 514/228.5; 544/57, 58.6, 115, 337, 346, 354, 356

[56] References Cited

U.S. PATENT DOCUMENTS 5,153,196 10/1992 McQuaid et al. ............ 514/250
5,559,106 9/1996 Jacobsen et al. ............ 514/81

FOREIGN PATENT DOCUMENTS 0 040 401 11/1981 European Pat. Off. .
WO 93/06103 4/1993 WIPO .
WO 93/20077 10/1993 WIPO .
WO 94/21639 9/1994 WIPO .
WO 94/26746 11/1994 WIPO .

OTHER PUBLICATIONS

P.L. Herrling, Synaptic Physiology of Excitatory Amino Acids, pp. 202–208 Arzeim–Forsch Drug Res. vol. 42, No. 2a (1992).

Primary Examiner—John M. Ford
Attorney, Agent, or Firm—Steve T. Zelson; Carol E. Rozek

[57] ABSTRACT

The present invention relates to [1,2,4]triazolo[4,3-a] quinoxalinone compounds of the formula

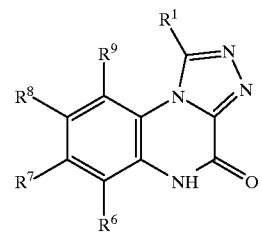

(I)

wherein $R^1$ is POX'X" or alkyl substituted with COX' or POX'X", and X' and X" independently are hydroxy or alkoxy, and $R^7$ is trifluoromethyl, and $R^6$, $R^8$ and $R^9$ independently are piperidino, piperazinyl, morpholino, or thiomorpholino, which rings are optionally substituted with one or more of phenyl or $C_{1-6}$-alkyl and phenyl optionally being substituted with $C_{1-6}$-alkoxy; and pharmaceutically acceptable salts thereof. The compounds of the present invention are useful in the treatment of indications caused by hyperactivity of the excitatory neurotransmitters.

9 Claims, No Drawings

[1,2,4]TRIAZOLO[4,3-A]QUINOXALINONE DERIVATIVES, THEIR PREPARATION AND USE

CROSS-REFERENCE TO RELATED APPLICATIONS

This application is a 35 U.S.C. 371 national application of PCT/DK95/00364 filed Mar. 21, 1996 and claims priority under 35 U.S.C. 119 of Danish application 1065/94 filed Sep. 16, 1994, the contents of which are fully incorporated by reference.

The present invention relates to therapeutically active heterocyclic compounds, a method of preparing the same, pharmaceutical compositions comprising the compounds, and a method of treating therewith.

More specifically, the invention relates to [1,2,4]triazolo[4,3-a]quinoxalinone derivatives, which are useful in the treatment of any indication caused by hyperactivity of excitatory amino acids.

Various related compounds are known from the prior art.

Thus, EP-A-0040401 generically describes inter alia triazoloquinoxalin-4-ones substituted at the triazolo ring with e.g. an alkyl, acyl or carbalkoxy group. These compounds are claimed to possess useful anti-hypertensive activity.

In U.S. Pat. No. 5,153,196 some excitatory amino acid receptor antagonists and methods for the use thereof are disclosed. The compounds conform inter alia to triazoloquinoxalinones having one substituent being H, alkyl, aromatic or $CF_3$ at the triazolo ring.

Further, international patent publication No. WO 93/20077 deals inter alia with fused quinoxalinone derivatives optionally substituted in the triazolo-ring with lower alkyl which may be substituted by mono- or di(lower alkyl)amino.

L-glutamic acid, L-aspartic acid and a number of other closely related amino acids have in common the ability to activate neurons in the central nervous system (CNS). Biochemical, electrophysiological and pharmacological studies have substantiated this and demonstrated that acidic amino acids are transmitters for the vast majority of excitatory neurons in the mammalian CNS.

Interaction with glutamic acid mediated neurotransmission is considered a useful approach in the treatment of neurological and psychiatric diseases. Thus, known antagonists of excitatory amino acids have shown potent anxiolytic (Stephens et al., Psychopharmacology,90, 143–147, 1985), anticonvulsant (Croucher et al., Science 216, 899–901, 1982) and muscle relaxant properties (Turski et al., Neurosci. Lett. 53, 321–326, 1985).

It has been suggested that accumulation of extracellular excitatory amino acids, followed by overstimulation of neurons, may explain the neuronal degenerations seen in neurological disorders such as amyotrophic lateral sclerosis, Parkinsonism, Alzheimer's disease, Huntington's disease, epilepsy, and deficiencies of mental and motor performance seen after conditions of brain ischemia, anoxia and hypoglycemia or head and spinal cord trauma (McGeer et al., Nature 263, 517–519, 1976; Simon et al., Science 226, 850–852, 1984; Wieloch, Science 230, 681–683, 1985; Faden et al., Science 244, 798–800, 1989; Turski et al., Nature 349, 414–418, 1991). Other possible indications are psychosis, muscle rigidity, emesis and analgesia.

Excitatory amino acids exert their actions via specific receptors located postsynaptically or presynaptically. Such receptors are at present conveniently subdivided into three groups bases on electrophysiological and neurochemical evidence: 1 the NMDA (N-methyl-D-aspartate) receptors, 2 the AMPA receptors, and 3 the kainate receptors. L-glutamic acid and L-aspartic acid probably activate all the above types of excitatory amino acid receptors and possibly other types as well.

The above mentioned classification of excitatory amino acid receptors into NMDA, AMPA, and kainate receptors is based primarily on the following electrophysiological and neurochemical findings.

1) N-methyl-D-aspartate (NMDA) receptors exhibit high selectivity for the excitant NMDA. Ibotenic acid, L-homocysteic acid, D-glutamic acid and trans-2,3-piperidine dicarboxylic acid (trans-2,3-PDA) exert a strong to moderate agonist activity on these receptors. The most potent and selective antagonists are the D-isomers of the 2-amino-5-phosphonocarboxylic acids, e.g. 2-amino-5-phosphono-valeric acid (D-APV) and 3-[(±)-2-carboxypiperazin-4-yl]-propyl-1-phosphonic acid (CPP), while moderate antagonist activity is shown by the D-isomers of long chain 2-amino dicarboxylic acids (e.g. D-2-aminoadipic acid) and long chain diaminodicarboxylic acids (e.g. diaminopimelic acid). The NMDA-induced synaptical responses have been extensively investigated in the mammalian CNS, especially in the spinal cord (J. Davies et al., J. Physiol. 297, 621–635, 1979) and the responses have been shown to be strongly inhibited by $Mg^{2+}$.

2) AMPA receptors are activated selectively by AMPA (2-amino-3-hydroxy-5-methyl-4-isoxazolepropionic acid), other potent agonists being quisqualic acid and L-glutamic acid. Glutamic acid diethyl ester (GDEE) is a selective but very weak antagonist of this site. AMPA receptors are relatively insensitive to $Mg^{2+}$.

Glutamate release has long been thought to play a major role in neuronal death resulting from cerebral ischemia (Benveniste, H. et al., J. Neurochem. 43, 1369–1374, 1984). It is well known that NMDA receptor evoked $Ca^{2+}$ influx is an important mechanism in ischemic neuronal cell loss. The non-NMDA receptor coupled ionophor is not permeable to calcium. However, the excitation by the Scaffer collaterals in the CA1 region is excerted by non-NMDA receptors, and this fact is of importance for the events in the postischemic period. Recent studies have shown that selective AMPA antagonists have neuroprotectant effects in global ischemia in the gerbil even when given several hours after reperfusion (Sheardown et al., Science 247, 571–574, 1990).

AMPA antagonists are therefore useful in the treatment of cerebral ischemia.

3) Kainate receptors. Excitatory responses to kainic acid are relatively insensitive to antagonism by NMDA-antagonists and by GDEE, and it has been proposed that kainic acid activates a third subclass of acidic amino acid receptor. Certain lactonized derivatives of kainic acid are selective antagonists (O. Goldberg et al., Neurosci. Lett. 23, 187–191, 1981) and the dipeptide 3-glutamyl-glycine also shows some selectivity for kainate receptors. $Ca^{2+}$ but not $Mg^{2+}$ is a strong inhibitor of kainic acid binding.

The affinity of a substance for one or more of the different types of excitatory amino acid receptors may be studied in simple binding experiments. In essence, the method involves incubation of a particular selected radiolabelled ligand and the particular specific substance to be investigated with brain homogenate which contains the receptor. Measurement of receptor occupancy is made by determination of the radioactivity bound to the homogenate and subtraction of non-specific binding.

AMPA receptor binding may be studied by using $^3$H-AMPA as radioligand.

The influence of glutamic acid analogues on secondary effects of glutamate receptor interactions may be studied in vitro by using the phenomenon of spreading depression in chicken retina. Such experiments will provide information as to the efficacies (agonist/antagonist) of the test substances. This is in contrast to binding studies, which only provide information on the affinities of the compounds for the receptor.

It has now been found that the compounds of the invention have affinity for the AMPA receptors and are antagonists in connection with this type of receptor which makes them useful in the treatment of any of the numerous indications caused by hyperactivity of excitatory amino acids, especially neuronal degeneration as are observed in amyotrophic lateral sclerosis, Huntington's chorea, Parkinson's disease, epilepsy and senile dementia or mental and motor dysfunctions seen after conditions of brain ischemia, oxygen deficiency, hypoglycemia and head and spinal cord trauma. Other possible indications are psychosis, muscle rigidity, emesis, acute and chronic inflammatory disease and analgesia.

The compounds of the invention are represented by the general formula I

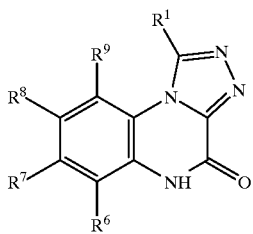

wherein

R$^1$ is POX'X" or straight or branched C$_{1-6}$-alkyl substituted with COX' or POX'X" and X' and X" independently are hydroxy or C$_{1-6}$-alkoxy, and R$^6$, R$^7$, R$^8$ and R$^9$ independently are hydrogen; C$_{1-6}$-alkyl; halogen; NH$_2$; NO$_2$; CN; CF$_3$; SO$_2$NY'Y"; COZ' wherein Z' is NY'Y" or C$_{1-6}$-alkyl, and Y' and Y" independently are hydrogen or C$_{1-6}$-alkyl; triazolyl; imidazolyl; piperidino; piperazinyl; morpholino; thiomorpholino, which rings are optionally substituted with one or more of phenyl or C$_{1-6}$-alkyl and phenyl optionally being substituted with C$_{1-6}$-alkoxy; and pharmaceutically acceptable salts thereof.

The term "C$_{1-6}$-alkyl" as used herein refers to a straight or branched, saturated hydrocarbon chain having 1–6 carbon atoms such as methyl, ethyl, n-propyl, isopropyl, n-butyl, 2-butyl, tert.butyl, 3-pentyl, neopentyl or n-hexyl.

The term "C$_{1-6}$-alkoxy" as used herein, alone or in combination, refers to a monovalent substituent comprising a C$_{1-6}$-alkyl group linked through an ether oxygen having its free valence bond from the ether oxygen, e.g. methoxy, ethoxy, propoxy, isopropoxy, cyclopropylmethoxy, butoxy, pentoxy.

The term "halogen" as used herein means fluorine, chlorine, bromine and iodine.

In a preferred embodiment of the invention R$^1$ is C$_{1-6}$-alkyl substituted with COX' or POX'X".

In another preferred embodiment of the invention R$^6$, R$^7$, R$^8$ and R$^9$ are independently hydrogen; chlorine; NO$_2$; CN; CF$_3$; piperidino; morpholino; thiomorpholino; piperazinyl; piperazinyl substituted with methyl, phenyl or methoxyphenyl; triazolyl disubstituted with methyl; imidazolyl disubstituted with methyl, ethyl, phenyl.

In yet another preferred embodiment of the invention R$^6$ and R$^9$ are hydrogen.

Preferred compounds of the invention are:

1-(Ethoxy-hydroxy-phosphorylmethyl)-8-(4-methyl-2-phenyl-1H-imidazol-1-yl)-7-trifluoromethyl[1,2,4]triazolo[4,3-a]quinoxalin-4(5H)-one;

8-(4-Methyl-2-phenyl-1H-imidazol-1-yl)-1-phosphonomethyl-7-trifluoromethyl[1,2,4]triazolo[4,3-a]quinoxalin-4(5H)-one;

1-(Ethoxy-hydroxy-phosphorylmethyl)-8-(2-ethyl-4-methyl-1H-imidazol-1-yl)-7-trifluoromethyl[1,2,4]triazolo[4,3-a]quinoxalin-4(5H)-one;

8-(2-Ethyl-4-methyl-1H-imidazol-1-yl)-1-phosphonomethyl-7-trifluoromethyl[1,2,4]triazolo[4,3-a]quinoxalin-4(5H)-one;

8-Morpholino-1-phosphonomethyl-7-trifluoromethyl[1,2,4]triazolo[4,3-a]quinoxalin-4(5H)-one;

8-Morpholino-1-(1-phosphonoethyl)-7-trifluoromethyl[1,2,4]triazolo[4,3-a]quinoxalin-4(5H)-one;

8-Piperidino-1-phosphonomethyl-7-trifluoromethyl[1,2,4]triazolo[4,3-a]quinoxalin-4(5H)-one;

1-(2-Ethoxycarbonylethyl)-8-morpholino-7-trifluoromethyl[1,2,4]triazolo-[4,3-a]quinoxalin-4(5H)-one;

1-(2-Carboxyethyl)-8-morpholino-7-trifluoromethyl[1,2,4]triazolo[4,3-a]quinoxalin-4(5H)-one.

Other preferred compounds of the invention are:

8-(2,4-Dimethyl-1H-imidazol-1-yl)-1-phosphonomethyl-7-trifluoromethyl-[1,2,4]triazolo[4,3-a]quinoxalin-4(5H)-one;

7-Cyano-8-(2,4-dimethyl-1H-imidazol-1-yl)-1-phosphonomethyl[1,2,4]triazolo[4,3-a]quinoxalin-4(5H)-one;

8-(2,4-Dimethyl-1H-imidazol-1-yl)-7-nitro-1-phosphonomethyl[1,2,4]triazolo[4,3-a]quinoxalin-4(5H)-one;

7-Cyano-8-(2-ethyl-4-methyl-1H-imidazol-1-yl)-1-phosphonomethyl[1,2,4]triazolo[4,3-a]quinoxalin-4(5H)-one;

7-Cyano-8-morpholino-1-phosphonomethyl[1,2,4]triazolo[4,3-a]quinoxalin-4(5H)-one;

8-Morpholino-7-nitro-1-phosphonomethyl[1,2,4]triazolo[4,3-a]quinoxalin-4(5H)-one;

7-Cyano-1-phosphonomethyl-8-thiomorpholino[1,2,4]triazolo[4,3-a]quinoxalin-4(5H)-one;

1-Phosphonomethyl-8-thiomorpholino-7-trifluoromethyl[1,2,4]triazolo[4,3-a]quinoxalin-4(5H)-one;

7-Cyano-1-phosphonomethyl-8-piperidino[1,2,4]triazolo[4,3-a]quinoxalin-4(5H)-one;

1-Phosphonomethyl-8-(piperazin-1-yl)-7-trifluoromethyl[1,2,4]triazolo[4,3-a]quinoxalin-4(5H)-one;

7-Cyano-1-phosphonomethyl-8-(piperazin-1-yl)[1,2,4]triazolo[4,3-a]quinoxalin-4(5H)-one;

8-(4-Phenylpiperazin-1-yl)-1-phosphonomethyl-7-trifluoromethyl[1,2,4]triazolo[4,3-a]quinoxalin-4(5H)-one;

7-Cyano-8-(4-phenylpiperazin-1-yl)-1-phosphonomethyl[1,2,4]triazolo[4,3-a]quinoxalin-4(5H)-one;

8-(4-(3-Methoxyphenyl)piperazin-1-yl)-1-phosphonomethyl-7-trifluoromethyl[1,2,4]triazolo[4,3-a]quinoxalin-4(5H)-one;

8-(4-(4-Methoxyphenyl)piperazin-1-yl)-1-phosphonomethyl-7-trifluoromethyl[1,2,4]triazolo[4,3-a]quinoxalin-4(5H)-one;

8-(2,4-Dimethyl-1H-imidazol-1-yl)-1-phosphonoethyl-7-trifluoromethyl[1,2,4]triazolo[4,3-a]quinoxalin-4(5H)-one;

7-Chloro-8-(2,4-dimethyl-1H-imidazol-1-yl)-1-phosphonomethyl[1,2,4]triazolo[4,3-a]quinoxalin-4(5H)-one;

8-(3,5-Dimethyl-1,2,4-triazol-1-yl)-1-phosphonomethyl-7-trifluoromethyl[1,2,4]triazolo[4,3-a]quinoxalin-4(5H)-one;

8-(4-Methylpiperazin-1-yl)-1-phosphonomethyl-7-trifluoromethyl[1,2,4]triazolo[4,3-a]quinoxalin-4(5H)-one;

1-(2-Carboxyethyl)-8-(2,4-dimethyl-1H-imidazol-1-yl)-7-trifluoromethyl[1,2,4]triazolo[4,3-a]quinoxalin-4(5H)-one;

1-(2-Carboxyethyl)-8-(2-ethyl-4-methyl-1H-imidazol-1-yl)-7-trifluoromethyl[1,2,4]triazolo[4,3-a]quinoxalin-4(5H)-one;

1-(2-Carboxyethyl)-7-cyano-8-(2,4-dimethyl-1H-imidazol-1-yl)[1,2,4]triazolo[4,3-a]quinoxalin-4(5H)-one;

1-(2-Carboxyethyl)-8-(4-phenylpiperazin-1-yl)-7-trifluoromethyl[1,2,4]triazolo[4,3-a]quinoxalin-4(5H)-one;

1-(2-Carboxyethyl)-8-(2,4-dimethyl-1H-imidazol-1-yl)-7-nitro[1,2,4]triazolo[4,3-a]quinoxalin-4(5H)-one;

1-(2-Carboxyethyl)-7-cyano-8-morpholino[1,2,4]triazolo[4,3-a]quinoxalin-4(5H)-one;

1-(2-Carboxyethyl)-8-morpholino-7-nitro[1,2,4]triazolo[4,3-a]quinoxalin-4(5H)-one;

1-(2-Carboxyethyl)-8-(4-methylpiperazin-1-yl)-7-trifluoromethyl[1,2,4]triazolo[4,3-a]quinoxalin-4(5H)-one;

1-(2-Carboxyethyl)-7-chloro-8-(2,4-dimethyl-1H-imidazol-1-yl)[1,2,4]triazolo[4,3-a]quinoxalin-4(5H)-one;

1-(2-Carboxyethyl)-8-(4-(4-methoxyphenyl)piperazin-1-yl)-7-trifluoromethyl[1,2,4]triazolo[4,3-a]quinoxalin-4(5H)-one;

1-(2-Carboxyethyl)-8-piperidino-7-trifluoromethyl[1,2,4]triazolo[4,3-a]quinoxalin-4(5H)-one.

The compounds of the invention may be present in different tautomeric forms. Therefore the invention includes all such tautomeric forms.

Another embodiment of the invention is pharmaceutically acceptable salts of [1,2,4]triazolo[4,3-a]quinoxalinone derivatives of formula I. Such salts include those derived from inorganic and organic acids such as hydrochloric acid, hydrobromic acid, acetic acid, sulfuric acid, nitric acid, oxalic acid, fumaric acid, tartaric acid, etc. Other salts include alkali metal salts such as sodium or potassium salts; alkaline earth metal salts such as calcium or magnesium salts; and ammonium salts.

Further, in another aspect the invention relates to a compound of the general formula (I) or a pharmaceutically acceptable salt thereof for use as a medicament, preferably for use as a medicament for treating an indication related to hyperactivity of exitatory neurotransmitters and particularly the AMPA receptors.

The invention also relates to a method of preparing the above mentioned compounds. The present compounds of formula I are prepared by a) alkylating a compound having the formula II

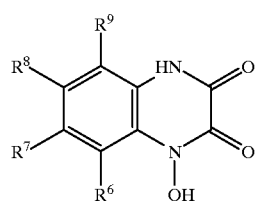
(II)

wherein $R^6$, $R^7$, $R^8$ and $R^9$ have the meanings defined above with benzylhalogenide to form a compound of the formula III

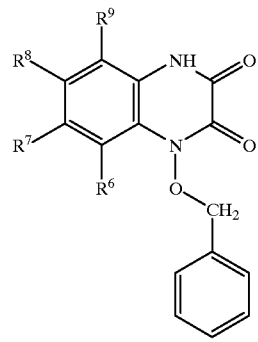
(III)

wherein $R^6$, $R^7$, $R^8$ and $R^9$ have the meanings defined above, and halogenating the compound to form a compound of the formula IV

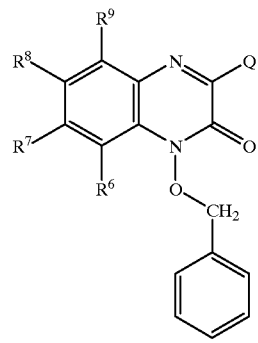
(IV)

wherein $R^6$, $R^7$, $R^8$ and $R^9$ have the meanings defined above and Q is Br, Cl, or I; and reacting the compound with hydrazine to form a compound of the formula V

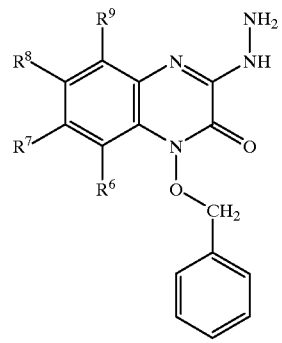
(V)

wherein $R^6$, $R^7$, $R^8$ and $R^9$ have the meanings defined above, and acylating the compound with an acylchloride with the general formula VI $R^1$—COCl (VI)

wherein $R^1$ has the meaning as defined above for a compound of the general formula I wherein X' and X" are $C_{1-6}$-alkoxy to form a compound of the formula VII

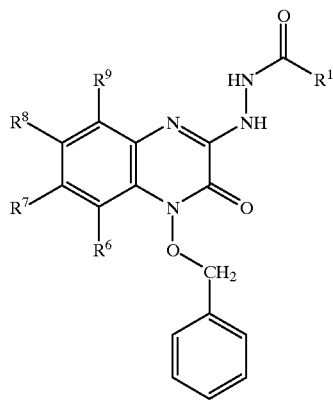

(VII)

wherein $R^1$, $R^6$, $R^7$, $R^8$ and $R^9$ have the meanings defined above, and hydrogenolysis of the compound to form a compound of the formula VIII

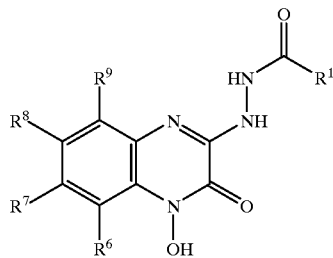

(VIII)

wherein $R^1$, $R^6$, $R^7$, $R^8$ and $R^9$ have the meanings defined above, and followed by thermal cyclization and simultaneous deoxygenation to form a compound of formula I, wherein X' and X" independently are hydroxy or $C_{1-6}$-alkoxy, or b) reacting a compound having the formula IX

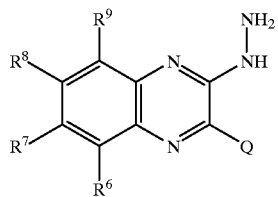

(IX)

wherein $R^6$, $R^7$, $R^8$ and $R^9$ have the meanings defined above, and Q is Br, Cl or I, with a compound of the general formula VI $R^1$—COCl     (VI)

wherein $R^1$ has the meaning as defined above for a compound of the general formula I wherein X' and X" are $C_{1-6}$-alkoxy to form a compound of the formula XI

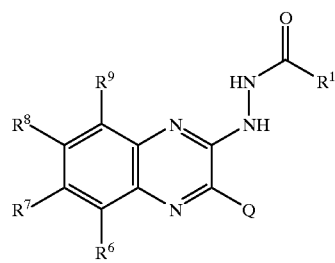

(XI)

wherein $R^1$, $R^6$, $R^7$, $R^8$ and $R^9$ have the meanings defined above, and Q is Br, Cl or I, and then either cyclization followed by hydrolysis or simultaneous cyclization and hydrolysis to form a compound of formula I, wherein X' and X" independently are hydroxy or $C_{1-6}$-alkoxy, or c) substituting a compound of the formula XII

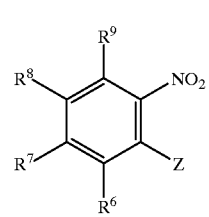

(XII)

wherein $R^6$, $R^7$, $R^8$ and $R^9$ have the meanings defined above and Z is either halogen or $C_{1-6}$-alkoxy with mono-, di-, or trimethoxy substituted benzylamine to form a compound of formula XIII

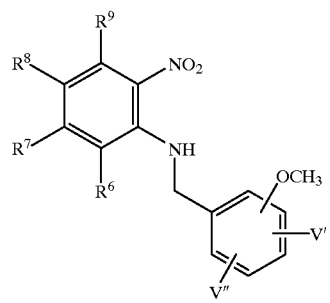

(XIII)

wherein $R^6$, $R^7$, $R^8$ and $R^9$ have the meanings defined above, and V' and V" independently are hydrogen or methoxy, and reacting the compound with ethyloxalylchloride to form a compound of formula XIV

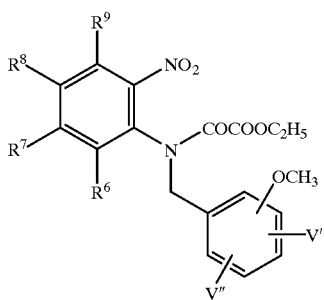

(XIV)

wherein $R^6$, $R^7$, $R^8$ and $R^9$ have the meanings defined above, and V' and V" independently are hydrogen or methoxy, and then either hydrogenation to form the intermediate cyclized N-hydroxy compound followed by deoxygenation or cyclization by hydrogenation to form a compound of formula XV

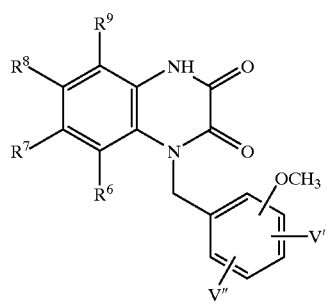

(XV)

wherein $R^6$, $R^7$, $R^8$ and $R^9$ have the meanings defined above, and V' and V" independently are hydrogen or methoxy, halogenating the compound of formula XV, reacting the resulting compound with hydrazine followed by acylating with an acylchloride of the general formula VI as defined above, and then cyclization to form a compound of formula XVI

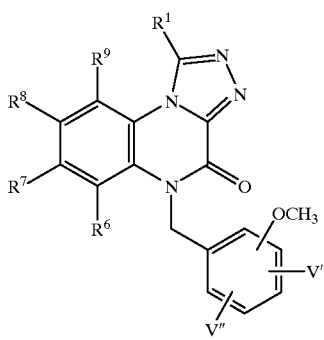

(XVI)

wherein $R^1$, $R^6$, $R^7$, $R^8$ and $R^9$ have the meanings defined above, and V' and V" independently are hydrogen or methoxy, and hydrolysis to form a compound of formula I, wherein X' and X" independently are hydrogen or $C_{1-6}$-alkoxy, or d) hydrolysing a compound of formula I, wherein X' and X" are $C_{1-6}$-alkoxy with aqueous base to form a compound of formula I, wherein X' is hydroxy, and X" is $C_{1-6}$-alkoxy, or e) reacting a compound of formula I, wherein X' is hydroxy or $C_{1-6}$-alkoxy, and X" is $C_{1-6}$-alkoxy with halotrimethylsilane to form a compound of formula I, wherein X' and X" are hydroxy.

Pharmaceutically acceptable salts may be prepared according to standard procedures by treating a compound of formula I with the appropriate acids or bases.

The starting materials for which the preparation is not described herein are either known compounds (e.g. from International appl. no. PCT-DK94/00170) or compounds which may be prepared in analogy with the preparation of known compounds or in analogy with known methods.

The pharmacological properties of the compounds of the present invention can be illustrated by determining their capability for displacing radioactively labelled 2-amino-3-hydroxy-5-methyl-4-isoxazolepropionic acid (AMPA) from the AMPA type receptors. The antagonistic properties of the compounds is demonstrated by their capability to antagonize quisqualic acid stimulated spreading depression in chicken retina.

The displacement activity of the compounds may be shown by determining the $IC_{50}$ value which represents the concentration ($\mu$M) which causes a displacement of 50% of the specific binding of $^3$H-AMPA.

The antagonism is measured by determining the $IC_{50}$ value which represents the concentration which produces a 50% maximal inhibition of quisqualic acid stimulated spreading depression in chicken retina.

$^3$H-AMPA Binding (Test 1)

500 $\mu$l of thawed rat cerebral cortical membrane homogenate in Tris-HCl (30 mM), $CaCl_2$ (2.5 mM) and KSCN (100 mM) pH 7.1 were incubated at 0° C. for 30 min. with 25 $\mu$l $^3$H-AMPA (5 nM final concentration) and the test compound and buffer. Nonspecific binding was determined by incubation with L-glutamic acid (600 $\mu$M final concentration). The binding reaction was terminated by adding 5 ml of ice-cold buffer followed by filtration through Whatman GF/C glass fibre filters and 2×5 ml wash with ice-cold buffer. Bound radioactivity was measured by scintillation counting. $IC_{50}$ was determined by Hill analysis of at least four concentrations of test compound.

Spreading Depression (Test 2)

Chicks (3–10 days old) were decapitated, the eyes enucleated and sectioned along the equatorial plane. After removal of the anterior chamber and the vitreous body, the posterior chamber of each eye was placed in a small petri dish containing a physiological saline solution (P.S.S.) of the following composition (mM) NaCl (100), KCl (6.0), $CaCl_2$ (1.0), $MgSO_4$ (1.0), $NaHCO_3$ (30), $NaH_2PO_4$ (1.0), glucose (20).

The solution was saturated with 100% $O_2$ and maintained at a temperature of 26° C.

The eyes were initially incubated in normal P.S.S. for 15–30 min. and then transferred to P.S.S. containing quisqualate (1 $\mu$g/ml). In this "stimulating solution" S.D.s start spontaneously usually from the edge of the retina, and can be easily observed by eye. The time taken for an S.D. to start in each eye was measured.

After a further 15 min. of incubation in normal P.S.S. the eyes were transferred to normal P.S.S. containing the test compound and incubated for 15 min. Thereafter the eyes were transferred to a "stimulating solution" containing the same concentration of the test compound. The time taken for an S.D. to start in each eye was measured again. The eyes were then placed back in normal P.S.S. and after 15 min. the time taken for S.D. to start was measured again, in order to assess the degree of recovery from any drug effects.

An increase in the time taken for S.D. to start of 30 seconds more than the control time is considered 100% inhibition of S.D. The drug effects therefore are expressed as the percentage maximum response obtained for a given dose. The test value can be quoted therefore as the concentration ($\mu$M) of test substance which produces a 50% maximal inhibition ($IC_{50}$).

Test results obtained by testing some compounds of the present invention are shown in the following table 1.

TABLE 1

| Compound of example | TEST 1 $IC_{50}$ $\mu$M | TEST 2 $IC_{50}$ $\mu$M |
|---|---|---|
| 2 | 0.39 | 0.40 |

The pharmaceutical preparations of compositions comprising the compounds of the invention may be administered to humans or animals by oral, rectal or parenteral route.

An effective amount of the active compound or a pharmaceutically acceptable salt thereof may be determined in accordance with the usual factors, such as the nature and severity of the condition and the weight of the mammal requiring treatment.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or colouring substances and the like, which do not deleteriously react with the active compounds.

Injectable solutions or suspensions, preferably aqueous solutions with the active compound dissolved in polyhydroxylated castor oil, are particularly suitable for parenteral administration.

Ampoules are convenient unit dosage forms.

Tablets, dragees, or capsules containing talc and/or a carrier or binder or the like are particularly suitable for oral administration. The carrier preferably is lactose and/or corn starch and/or potato starch.

A syrup, elixir, or the like can be used in the cases where a sweetened vehicle can be employed or is desired.

Generally, the compounds of this invention are dispensed in unit dosage form comprising 0.5–1000 mg of active ingredient in or together with a pharmaceutically acceptable carrier per unit dosage.

The dosage of the compounds according to this invention is 1–500 mg/day, e.g. about 50–100 mg per dose, when administered to patients, e.g. humans, as a drug.

A typical tablet which may be prepared by conventional tabletting techniques contains:

| Core: | |
|---|---|
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | 1 mg |
| Coating: | |
| HPMC | approx. 9 mg |

-continued

| | |
|---|---|
| *Mywacett ® 9-40T | approx. 0.9 mg |

*Acylated monoglyceride used as plasticizer for film-coating

The free compounds of the present invention which form alkali metal or alkaline earth metal salts may be employed in such salt form. Such alkali metal or earth alkali metal salts are ordinarily formed by reacting the compound with an equivalent amount or excess of the selected alkali metal or earth alkali metal as the hydroxide, frequently and suitably by admixture in the presence of a neutral solvent, from which the salt may be precipitated or recovered in other conventional manner, e.g. by evaporation. Administration of a compound of the invention is often preferably in the form of a pharmaceutically acceptable water-soluble alkali metal or earth alkali metal salt thereof, and orally, rectally, or parenterally in the form of a pharmaceutical composition wherein it is present together with a pharmaceutically acceptable liquid or solid carrier or diluent.

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective AMPA antagonistic amount of the active ingredient commensurate with the intended daily dosage range to be employed. Tablets containing 1–500 mg of active ingredient or, more specified 10–200 mg, per tablet, are accordingly suitable representative unit dosage forms.

Due to their high degree of AMPA antagonistic activity and their low toxicity, together presenting a most favourable therapeutic index, the compounds of the invention may be administered to a subject, e.g. a living animal body, in need of such treatment, elimination, alleviation, or amelioration of an indication which is sensitive to a change in the AMPA receptor condition, e.g. sclerosis, Parkinsonism, Alzheimer's disease, Huntington's disease, epilepsy, deficiencies seen after ischemia, anoxia, hypoglycemia, head and spinal cord trauma, psychosis, muscle rigidity, emesis and analgesia, often preferably in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Suitable dosage ranges are 1–500 mg daily, preferably 10–200 mg daily, and especially 50–100 mg daily, depending as usual upon the exact mode of administration, form in which administered, the indication towards which the administration is directed, the subject involved and the body weight of the subject involved, and the preference and experience of the physician or veterinarian in charge.

Such method of treating may be described as the treatment of an indication caused by or related to hyperactivity of the excitatory neurotransmitters, and particularly the AMPA receptors in a subject in need thereof, which comprises the step of administering to the said subject a neurologically effective amount of an AMPA antagonistic compound of the invention, or a pharmaceutically acceptable salt thereof.

Furthermore, the present invention relates to the use of a compound of the invention for preparing a medicament for treating an indication caused by or related to hyperactivity of the excitatory neurotransmitters, and particularly the AMPA receptors in a subject in need thereof.

The invention will now be described in further detail with reference to the following examples:

EXAMPLE 1

1-(Ethoxy-hydroxy-phosphorylmethyl)-8-(4-methyl-2-phenyl-1H-imidazol-1-yl)-7-trifluoromethyl[1,2,4]triazolo[4,3-a]quinoxalin-4(5H)-one a. 1-Benzyloxy-3-chloro-6-(4-methyl-2-phenyl-1H-imidazol-1-yl)-7-trifluoromethylquinoxalin-2(1H)-one, hydrochloride A solution of 20% phosgene in toluene (18.2 ml, 35 mmol) was added dropwise to a stirred solution of 1-benzyloxy-6-(4-methyl-2-phenyl-1H-imidazol-1-yl)-7-trifluoromethylquinoxaline-2,3(1H,4H)-dione (8.8 g, 17.5 mmol) in 100 ml of dry N,N-dimethylformamide at 0° C. The mixture was stirred at room temperature overnight and the precipitated solid was isolated by filtration and washed with ether to give 8.0 g (84%) of the title compound.

$^1$H-NMR (DMSO-$d_6$): δ 6 2.42 (s, 3H), 5.35 (s, 2H), 7.30–7.61 (m, 10H), 7.62 (s, 1H), 7.75 (s, 1H), 8.48 (s, 1H).

b. 1-Benzyloxy-3-hydrazino-6-(4-methyl-2-phenyl-1H-imidazol-1-yl)-7-trifluoromethylquinoxalin-2(1H)-one A mixture of 1-benzyl-3-chloro-6-(4-methyl-2-phenyl-1H-imidazol-1-yl)-7-trifluoromethylquinoxalin-2(1H)-one hydrochloride (2.0 g, 3.6 mmol) and hydrazine hydrate (0.74 ml, 15 mmol) in 40 ml of dichloromethane was stirred at 0° C. for 1 h and evaporated to dryness in vacuo. The residue was triturated with water to give 1.59 g (87%) of the title compound. M.p. 127–130° C.

$^1$H-NMR (DMSO-$d_6$): δ 2.21 (s, 1H), 5.34 (s, 2H), 7.01 (s, 1H), 7.18 (s, 1H), 7.27 (s, 5H), 7.37–7.45 (m, 3H), 7.48 (s, 1H), 7.51–7.60 (m, 2H).

c. 1-Benzyloxy-3-[2-[(diethoxyphosphoryl)acetyl]hydrazino]-6-(4-methyl-2-phenyl-1H-imidazol-1-yl)-7-trifluoromethylquinoxalin-2(1H)-one A solution of (diethoxyphosphoryl)acetyl chloride (0.67 g, 3.1 mmol) in 20 ml of dry tetrahydrofuran was added dropwise to a stirred solution of 1-benzyloxy-3-hydrazino-6-(4-methyl-2-phenyl-1H-imidazol-1-(-yl)-7-trifluoromethylquinoxalin-2(1H)-one (1.52 g, 3.0 mmol) and dry triethylamine (0.43 ml, 3.1 mmol) in 50 ml of dry tetrahydrofuran.

The mixture was stirred overnight at room temperature and then evaporated to dryness in vacuo. The residue was triturated with water giving 1.8 g (88%) of the title compound. M.p.>90° C. decomp.

$^1$H-NMR (DMSO-$d_6$): δ 1.10–1.21 (m, 6H), 2.20 (s, 3H), 2.99 (d, 2H), 4.01 (quint., 4H), 5.40 (s, 2H), 7.04 (s, 1H), 7.24 (s, 6H), 7.37–7.46 (m, 3H), 7.50–7.62 (m, 3H), 10.26 (s, 1H), 10.38 (s, 1H).

d. 3-[2-[(Diethoxyphosphoryl)acetyl]hydrazino]-1-hydroxy-6-(4-methyl-2-phenyl-1H-imidazol-1-yl)-7-trifluoromethylquinoxalin-2(1H)-one A suspension of 1-benzyloxy-3-[2-[(diethoxyphosphoryl)acetyl]hydrazino]-6-(4-methyl-2-phenyl-1H-imidazol-1-yl)-7-trifluoromethylquinoxalin-2(1H)-one (1.8 g, 2.6 mmol) and 50 mg of 5% palladium on carbon in 50 ml of ethanol was hydrogenated at room temperature and atmospheric pressure for 9 h. The catalyst was removed by filtration, the filtrate evaporated to dryness in vacuo and the residue finally triturated with ether to give 1.51 g (97%) of the title compound. M.p.>177° C. decomp. $^1$H-NMR (DMSO-$d_6$): δ 1.10–1.22 (m, 6H), 2.23 (s, 3H), 2.98 (d, 2H), 4.00 (quint., 4H), 7.12 (s, 1H), 7.18–7.30 (m, 5H), 7.31 (s, 1H), 7.92 (s, 1H), 10.24 (s, 2H), 12.52 (br. s, 1H).

e. 1-(Ethoxy-hydroxy-phosphorylmethyl)-8-(4-methyl-2-phenyl-1H-imidazol-1-yl)-7-trifluoromethyl[1,2,4]triazolo[4,3-a]quinoxalin-4(5H)-one A solution of 3-[2-[(diethoxyphosphoryl)acetyl]hydrazino]-1-hydroxy-6-(4-methyl-2-phenyl-1H-imidazol-1-yl)-7-trifluoromethylquinoxalin-2(1H)-one (1.5 g, 2.5 mmol) and triphenylphosphine (1.3 g, 5 mmol) in 50 ml of glacial acetic acid was stirred overnight at 120° C.

The cooled mixture was filtered and the isolated product was washed with ether to give 0.64 g (48%) of the title compound. M.p. 303–308° C.

$^1$H-NMR (DMSO-$d_6$): δ 1.10 (t, 3H), 2.25 (s, 3H), 3.87 (quint., 2H), 3.97 (d, 2H), 7.12 (s, 1H), 7.14–7.45 (m, 5H), 7.72 (s, 1H), 8.62 (s, 1H), 12.4 (s, 1H).

EXAMPLE 2

8-(4-Methyl-2-phenyl-1H-imidazol-1-yl)-1-phosphonomethyl-7-trifluoromethyl[1,2,4]triazolo[4,3-a]quinoxalin-4(5H)-one Bromotrimethylsilane (1 ml, 7 mmol) was added dropwise to a stirred solution of 1-(ethoxy-hydroxy-phosphorylmethyl)-8-(4-methyl-2-phenyl-1H-imidazol-1-yl)-7-trifluoromethyl[1,2,4]triazolo[4,3-a]quinoxalin-4(5H)-one (500 mg, 0.94 mmol) in 20 ml of dry N,N-dimethylformamide.

The solution was stirred at room temperature overnight and evaporated to dryness in vacuo. The residue was triturated with 10 ml of water and the precipitated solid was isolated by filtration. Washing with a small amount of water and ethanol gave 0.45 g (95%) of the pure title compound. M.p. 321–325° C.

$^1$H-NMR (DMSO-$d_6$): δ 2.35 (s, 3H), 3.93 (d, 2H), 7.22–7.52 (m, 6H), 7.74 (s, 1H), 8.79 (s, 1H), 12.4 (s, 1H).

EXAMPLE 3

1-(Ethoxy-hydroxy-phosphorylmethyl)-8-(2-ethyl-4-methyl-1H-imidazol-1-yl)-7-trifluoromethyl[1,2,4]triazolo[4,3-a]quinoxalin-4(5H)-one The title compound was prepared from 1-benzyloxy-6-(2-ethyl-4-methyl-1H-imidazol-1-yl)-7-trifluoromethylquinoxaline-2,3(1H,4H)-dione by a method analogous to the method described in example 1, except that the final product (theoretically 10.8 mmol) was worked up in the following way. To the cooled solution was added 100 ml of dichloromethane and 100 ml of ether. The precipitated solid was isolated by filtration and extracted with boiling water (2×100 ml). The aqueous phase was concentrated to about 100 ml and cooled on an ice-bath. The resulting precipitate was isolated by filtration and dried to give 0.90 g (17%) of the title compound.

$^1$H-NMR (CF$_3$COOD): δ 1.38 (t, 3H), 1.45 (t, 3H), 2.51 (s, 3H), 2.72–3.10 (m, 2H), 4.31 (quint., 2H), 4.58 (dd, 2H (partially exchanged)), 7.22 (s, 1H), 8.32 (s, 1H), 9.00 (s, 1H).

EXAMPLE 4

8-(2-Ethyl-4-methyl-1H-imidazol-1-yl)-1-phosphonomethyl-7-trifluoromethyl[1,2,4)triazolo[4,3-a]quinoxalin-4(5H)-one The title compound was prepared from 1-(ethoxy-hydroxy-phosphorylmethyl)-8-(2-ethyl-4-methyl-1H-imidazol-1-yl)-7-trifluoromethyl[1,2,4]triazolo[4,3-a]quinoxalin-4(5H)-one (870 mg, 1.8 mmol) by a method analogous to the method described in example 2. Yield: 710 mg (86%). M.p.>300° C.

$^1$H-NMR (DMSO-$d_6$): δ 1.10 (t, 3H), 2.20 (s, 3H), 2.27–2.77 (m, 2H), 3.62–3.95 (m, 2H), 7.07 (s, 1H), 7.85 (s, 1H), 8.55 (s, 1H); MS (FAB): m/e 457 (MH$^+$). ($C_{17}H_{16}N_6F_3O_4P.\frac{1}{2}H_2O$)

| Calc.: | C 43.88 | H 3.68 | N 18.06 |
| --- | --- | --- | --- |
| Found: | C 44.07 | H 3.56 | N 18.02 |

EXAMPLE 5

8-Morpholino-1-phosphonomethyl-7-trifluoromethyl
[1,2,4]triazolo[4,3-a]quinoxalin-4(5H)-one a. 1-(Ethoxy-hydroxy-phosphorylmethyl)-8-morpholino-7-trifluoromethyl[1,2,4]triazolo[4,3-a]quinoxalin-4(5H)-one The title compound was prepared from 1-benzyloxy-6-morpholino-7-trifluoromethylquinoxaline-2,3(1H,4H)-dione by a method analogous to the method described in example 1, except that the final product was isolated in the following way. The mixture was evaporated to dryness in vacuo and the residue was taken up in a mixture of 200 ml of dichloromethane and 50 ml of chloroform. The resulting solution was extracted with water (6×100 ml) and the aqueous solution was evaporated to dryness under reduced pressure by azeotropic distillation with 1-propanol to give the crude product, which was used without further purification in the following step.

b. 8-Morpholino-1-phosphonomethyl-7-trifluoromethyl[1,2,4]triazolo[4,3-a]quinoxalin-4(5H)-one The title compound was prepared from crude 1-(ethoxy-hydroxy-phosphorylmethyl)-8-morpholino-7-trifluoromethyl[1 2,4]triazolo[4,3-a]quinoxalin-4(5H)-one by a method analogous to the method described in example 2. M.p.>300° C decomp. (ethanol).

$^1$H-NMR (DMSO-d$_6$): δ 2.9–3.03 (m, 4H), 3.66–3.78 (m, 4H), 3.98 (d, 2H), 7.68 (s, 1H), 8.39 (s, 1H), 12.18 (s, 1H).

EXAMPLE 6

8-Morpholino-1-(1-phosphonoethyl)-7-trifluoromethyl[1,2,4]triazolo[4,3-a]quinoxalin-4 (5H)-one a. 1-(1-(Ethoxy-hydroxy-phosphorylmethyl)-8-morpholino-7-trifluoromethyl[1,2,4]triazolo[4,3-a]quinoxalin-4(5H)-one The title compound was prepared from 1-benzyloxy-6-morpholino-7-trifluoromethylquinoxaline-2,3(1H,4H)-dione by a method analogous to the method described in example 5, except that 2-(diethoxyphosphoryl)propionyl chloride was used instead of (diethoxyphosphoryl)acetyl chloride. The crude product was used without further purification in the following step.

b. 8-Morpholino-1-(1-phosphonoethyl)-7-trifluoromethyl[1,2,4]triazolo[4,3-a]quinoxalin-4(5H)-one The title compound was prepared from crude 1-(1-(ethoxy-hydroxy-phosphorylmethyl)-8-morpholino-7-trifluoromethyl[1,2,4]triazolo[4,3-a]quinoxalin-4(5H)-one by a method analogous to the method described in example 2, except that the final product was purified by column chromatography. M.p.>300° C. decomp.

$^1$H-NMR (DMSO-d$_6$): δ 1.73 (dd, 3H), 2.87–3.02 (m, 4H), 3.68–3.78 (m, 4H), 4.11–4.38 (m, 1H), 7.68 (s, 1H), 8.38 (s, 1H), 12.18 (s, 1H).

EXAMPLE 7

8-Piperidino-1-phosphonomethyl-7-trifluoromethyl
[1,2,4]triazolo[4,3-a]quinoxalin-4(5H)-one a. 1-(Ethoxy-hydroxy-phosphorylmethyl)-8-piperidino-7-trifluoromethyl[1,2,4]triazolo[4,3-a]quinoxalin-4(5H)-one The title compound was prepared from 1-benzyloxy-6-piperidino-7-trifluoromethylquinoxaline-2,3(1H,4H)-dione by a method analogous to the method described in example 3, except that the crude product was used without further purification in the following step.

b. 8-Piperidino-1-phosphonomethyl-7-trifluoromethyl[1,2,4]triazolo[4,3-a]quinoxalin-4(5H)-one The title compound was prepared from crude 1-(ethoxy-hydroxy-phosphorylmethyl)-8-piperidino-7-trifluoromethyl[1,2,4]triazolo(4,3-a]quinoxalin-4(5H)-one by a method analogous to the method described in example 2. $^1$H-NMR (DMSO-d$_6$): δ 1.48–1.72 (m, 6H), 2.83–2.98 (m, 4H), 3.90 (d, 2H), 7.65 (s, 1H), 8.32 (s, 1H), 12.12 (s, 1H).

EXAMPLE 8

1-(2-Ethoxycarbonylethyl)-8-morpholino-7-trifluoromethyl[1,2,4]triazolo[4,3-a]quinoxalin-4 (5H)-one The title compound was prepared from 1-benzyloxy-6-morpholino-7-trifluoromethylquinoxaline-2,3(1H,4H)-dione and ethyl succinylchloride by a method analogous to the method described in example 1, except that the final product was worked up in the following way. The cooled mixture was evaporated to dryness in vacuo and purified by flash-chromatography successively with dichloromethane and ethyl acetate. Trituration with ether afforded the pure product. M.p. 204–210° C.

$^1$H-NMR (DMSO-d$_6$): δ 1.22 (t, 3H), 2.88–3.00 (m, 4H), 3.02 (t, 2H), 3.61–3.82 (m, 6H), 4.12 (q, 2H), 7.71 (s, 1H), 7.99 (s, 1H), 12.2 (br. s, 1H).

EXAMPLE 9

1-(2-Carboxyethyl)-8-morpholino-7-trifluoromethyl
[1,2,4]triazolo[4,3-a]quinoxalin-4(5H)-one A suspension of 1-(2-ethoxycarbonylethyl)-8-morpholino-7-trifluoromethyl[1,2,4]triazolo[4,3-a] quinoxalin-4(5H)-one (365 mg, 0.83 mmol) in 10 ml of 2N potassium hydroxide was stirred at room temperature for 3 h.

The resulting solution was filtered and the filtrate was acidified with 4M hydrochloric acid to give a precipitate. The product was isolated by filtration, washed with water and dried to give the title compound. M.p. 170–176° C. $^1$H-NMR (DMSO-d$_6$): δ 6 2.88–3.02 (m, 6H), 3.67 (t, 2H), 3.68–3.80 (m, 4H), 7.71 (s, 1H), 7.99 (s, 1H), 12.26 (br. s, 1H).

What is claimed is:

1. [1,2,4]Triazolo[4,3-a]quinoxalinone compounds of the formula I

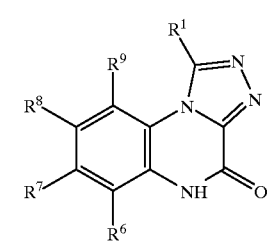
(I)

wherein $R^1$ is POX'X" or straight or branched $C_{1-6}$-alkyl substituted with COX' or POX'X", and X' and X" independently are hydroxy or $C_{1-6}$-alkoxy, and $R^6$, $R^8$ and $R^9$ independently are piperidino; piperazinyl; morpholino; or thiomorpholino, which rings are optionally substituted with one or more of phenyl or $C_{1-6}$-alkyl and phenyl optionally being substituted with $C_{1-6}$-alkoxy; or $R^6$ and $R^9$ independently are hydrogen; and $R^7$ is trifluoromethyl; and pharmaceutically acceptable salts thereof.

2. A compound according to claim 1 wherein $R^1$ is $C_{1-6}$-alkyl substituted with COX' or POX'X".

3. A compound according to claim 1 wherein $R^6$, $R^8$ and $R^9$ independently are piperidino; morpholino; thiomorpholino; piperazinyl; or piperazinyl substituted with methyl, phenyl or methoxyphenyl.

4. A compound according to claim 1 which is

8-Morpholino-1-phosphonomethyl-7-trifluoromethyl[1,2,4]triazolo[4,3-a]quinoxalin-4(5H)-one;

8-Morpholino-1-(1-phosphonoethyl)-7-trifluoromethyl[1,2,4]triazolo[4,3-a]quinoxalin-4(5H)-one;

8-Piperidino-1-phosphonomethyl-7-trifluoromethyl[1,2,4]triazolo[4,3-a]quinoxalin-4(5H)-one;

1-(2-Ethoxycarbonylethyl)-8-morpholino-7-trifluoromethyl[1,2,4]triazolo[4,3-a]quinoxalin-4(5H)-one; or 1-(2-Carboxyethyl)-8-morpholino-7-trifluoromethyl[1,2,4]triazolo[4,3-a]quinoxalin-4(5H)-one.

5. A pharmaceutical composition comprising as active component a compound according to claim 1 or a pharmaceutically acceptable salt thereof and a pharmaceutically acceptable carrier or diluent.

6. A pharmaceutical composition according to claim 5 in the form of a dosage unit containing about 10–200 mg of the active compound.

7. A method of treating neuronal degeneration comprising administering to a subject in need thereof a neurologically effective AMPA antagonistic amount of a compound according to claim 1 or a pharmaceutically acceptable salt thereof.

8. A method according to claim 7, wherein the indication is related to cerebral ischemia.

9. A method of preparing the compounds of formula I according to claim 1, which comprises a) alkylating a compound having the formula II

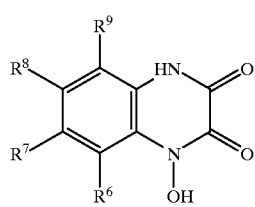

(II)

wherein $R^6$, $R^7$, $R^8$ and $R^9$ have the meanings defined above with benzylhalogenide to form a compound of the formula III

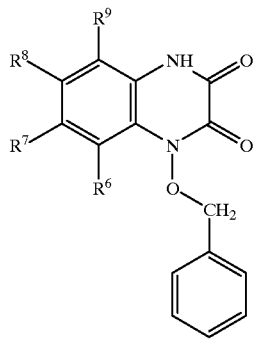

(III)

wherein $R^6$, $R^7$, $R^8$ and $R^9$ have the meanings defined above, and halogenating the compound to form a compound of the formula IV

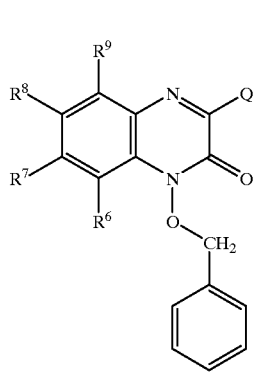

(IV)

wherein $R^6$, $R^7$, $R^8$ and $R^9$ have the meanings defined above and Q is Br, Cl or I; and reacting the compound with hydrazine to form a compound of the formula V

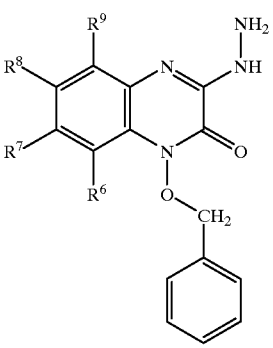

(V)

wherein $R^6$, $R^7$, $R^8$ and $R^9$ have the meanings defined above, and acylating the compound with an acylchloride with the general formula VI $R^1$—COCl (VI)

wherein $R^1$ has the meaning as defined above for a compound of the general formula I wherein X' and X" are $C_{1-6}$-alkoxy to form a compound of the formula VII

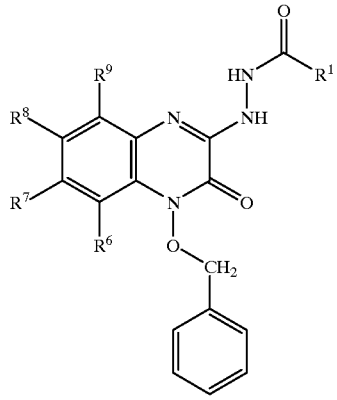
(VII)

wherein $R^1$, $R^6$, $R^7$, $R^8$ and $R^9$ have the meanings defined above, and hydrogenolysis of the compound to form a compound of the formula VIII

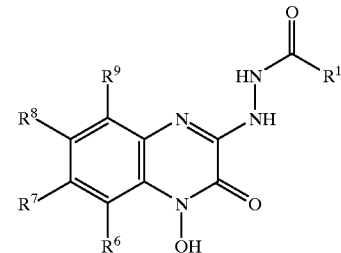
(VIII)

wherein $R^1$, $R^6$, $R^7$, $R^8$ and $R^9$ have the meanings defined above, and followed by thermal cyclization and simultaneous deoxygenation to form a compound of formula I, wherein X' and X" independently are hydroxy or $C_{1-6}$-alkoxy.

* * * * *